(12) United States Patent
Wyckoff

(10) Patent No.: US 7,198,608 B2  
(45) Date of Patent: Apr. 3, 2007

(54) APPENDAGE COVER WITH INFLATABLE RING AND METHOD OF USING SAME

(75) Inventor: Andrew K. Wyckoff, Carlisle, IA (US)

(73) Assignee: Wy-Tech, Inc., Des Moines, IA (US)

( * ) Notice: Subject to any disclaimer, the term of this patent is extended or adjusted under 35 U.S.C. 154(b) by 0 days.

(21) Appl. No.: 11/092,507

(22) Filed: Mar. 28, 2005

(65) Prior Publication Data

US 2006/0217646 A1    Sep. 28, 2006

(51) Int. Cl. *A61F 5/00* (2006.01)

(52) U.S. Cl. .......................................... 602/3

(58) Field of Classification Search ............. 602/75, 602/76, 77, 60, 61; 128/869, 876, 877, 878, 128/882; 606/201, 203
See application file for complete search history.

(56) References Cited

U.S. PATENT DOCUMENTS

| | | | | |
|---|---|---|---|---|
| 1,117,725 A | * | 11/1914 | Tullis | 623/31 |
| 2,582,648 A | * | 1/1952 | Mowbray | 36/8.1 |
| 3,548,819 A | * | 12/1970 | Davis et al. | 602/14 |
| 3,643,656 A | * | 2/1972 | Young | 128/90 |
| 3,659,599 A | | 5/1972 | McLaughlin | |
| 3,785,374 A | * | 1/1974 | Lipson | 128/82 |
| 4,098,268 A | | 7/1978 | Scott | |
| 4,530,350 A | | 7/1985 | Brown et al. | |
| 4,610,245 A | | 9/1986 | Biearman | |
| 4,639,945 A | * | 2/1987 | Betz | 2/22 |
| 4,911,151 A | * | 3/1990 | Rankin | 128/82 |
| 4,920,971 A | * | 5/1990 | Blessinger | 600/492 |
| D309,019 S | | 7/1990 | Holden | |
| 4,966,135 A | | 10/1990 | Renfrew | |
| 4,986,265 A | | 1/1991 | Caponi | |
| 5,063,919 A | * | 11/1991 | Silverberg | 128/82 |
| D323,217 S | | 1/1992 | Holden | |
| 5,190,489 A | * | 3/1993 | Yeung | 441/122 |
| 5,314,496 A | * | 5/1994 | Harrris | 623/31 |
| 5,314,497 A | * | 5/1994 | Fay | 623/34 |
| 5,342,286 A | * | 8/1994 | Kelly | 602/3 |
| 5,342,287 A | * | 8/1994 | Jernoiu | 602/3 |
| 5,526,536 A | * | 6/1996 | Cartmill | 2/161.7 |

(Continued)

FOREIGN PATENT DOCUMENTS

WO    WO9806353    *    2/1998

OTHER PUBLICATIONS

Broken Beauties (www.brokenbeauties.com); Shower-Beauties Waterproof Cast Cover; bathing aids for the fashion, comfort and healing of broken bones.

*Primary Examiner*—Kim M. Lewis  
(74) *Attorney, Agent, or Firm*—Brian J. Laurenzo; Jason M. Hunt (57) ABSTRACT

A cover is described for providing a protected area on a user's arm or leg, and especially over a cast on the arm or leg. The cover includes a sheath portion with an open end and a closed end. A user's arm is placed within the sheath. An inflatable ring is cooperable with the open end of the sheath to create a seal above an area of the arm or leg that is to be protected. An adhesive strip may be provided on the outside of the ring to adhere to a free end of the sheath.

17 Claims, 5 Drawing Sheets

U.S. PATENT DOCUMENTS

| | | |
|---|---|---|
| 5,728,052 A | 3/1998 | Meehan |
| 5,817,038 A | 10/1998 | Orange et al. |
| 5,865,772 A * | 2/1999 | George .......................... 602/3 |
| D406,897 S | 3/1999 | Agati et al. |
| 5,882,320 A * | 3/1999 | Peterson ........................ 602/3 |
| 6,126,621 A | 10/2000 | Aceves |
| 6,189,967 B1 * | 2/2001 | Short .................... 297/180.14 |
| 6,202,213 B1 | 3/2001 | Georgick |
| 2005/0171445 A1 * | 8/2005 | Millay et al. ................ 600/499 |

* cited by examiner

Fig. 13

APPENDAGE COVER WITH INFLATABLE RING AND METHOD OF USING SAME

FIELD OF INVENTION

This invention relates generally to protective covers for injured arms and legs, and more particularly to a water proof covering with an inflatable ring for use on arms and legs.

BACKGROUND

When a person fractures a bone in one of their limbs, such as an arm bone, leg bone, or a bone in the hand or foot, it is common for that limb, or portion of the limb to be immobilized in a cast. Traditionally these casts have been made out of plaster, and more recently fiberglass or other composites. In any event, it is generally desirable to keep the cast dry. This can create a problem for the person wearing the cast who wants to shower, bath, or participate in other activities that could expose the cast to water or other liquids.

As a result, people have commonly resorted to using plastic bags bound with rubber bands or string to provide a protective cover for the cast. This has not been a satisfactory solution to the problem. The bags are not shaped appropriately, and therefore, there is commonly bunching of the bag around the cast. This can lead to gaps which make the cover susceptible to leaks. Furthermore, it is unsightly and awkward. Attaching the rubber band or other binding can be awkward and difficult, especially when it is being applied to an arm, such that the user only has one hand available to use in attaching the binding. Furthermore, the bag can make it difficult to have independent use of the fingers. The rubber bands or other fasteners that have been used can be uncomfortable and cut off circulation.

Therefore, there is a need for a cover that can be used to protect casts, and other injuries, on arms and legs. Preferably, the cover will keep the user's cast dry and free from other contaminants. It should be comfortable to wear, and easy to attach, even if the user does not have use of both hands. Preferably the device will allow the user free use of his or her fingers. The device should be largely free from bunching and gaps, and should most preferably be adjustable to the length desired by the user.

Therefore, it is an object of the present invention to provide a light-weight cast cover that is simple to attach, comfortable to wear, and which will keep a cast dry during activities such as bathing or showering.

SUMMARY OF THE INVENTION

According to one embodiment, the present invention provides a cover assembly comprising a waterproof sheath portion having a closed end and an open end for insertion of a limb, and an inflatable ring for holding a portion of the waterproof sheath in close engagement with the limb when inflated. The inflatable ring can be slid to a desired distance spaced apart from the closed end of the sheath to provide a protected portion between the inflatable ring and the closed end of the sheath. The closed end of the sheath may include individual finger portions for engagement with a user's fingers. The inflatable ring may include an adhesive strip for adhering to a portion of the sheath that extends beyond the protected portion.

According to another embodiment, the present invention provides a method of protecting a portion of a limb. A waterproof sheath is placed over the limb, including the portion to be protected. An inflatable ring is placed over sheath at a location above the location to be protected. The ring is inflated to hold the waterproof sheath in close contact with the limb, and thereby seal the area of the limb that is distal from the ring.

DETAILED DESCRIPTION OF PREFERRED EMBODIMENTS

Figure 1:
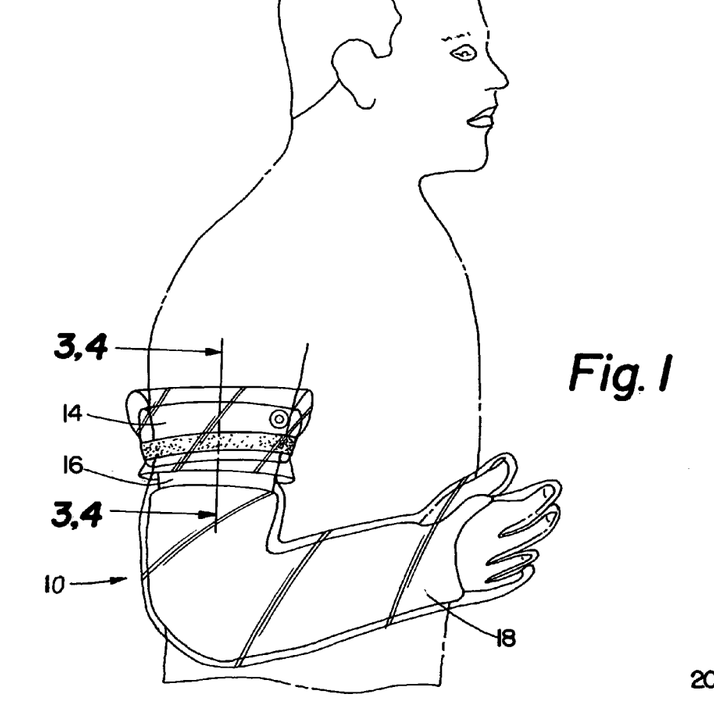
FIG. 1 is a perspective view showing a cover and inflatable ring according to one embodiment of the present invention in place on the arm of a user protecting a cast.

FIG. 1 shows an arm cover assembly 10 according to a preferred embodiment of the present invention in use. The arm cover assembly 10 includes a waterproof glove 12 and an inflatable ring 14. In use as shown in FIG. 1, the glove 12 covers the lower portion of a user's arm 16, and especially a cast 18 on the arm 16. The inflated ring 14 provides a seal against the upper portion of the user's arm 16 to create a barrier against water or other contaminants getting to the cast 18. The arm cover assembly 10 is light weight, easy to attach, and comfortable to wear.

Figure 2:
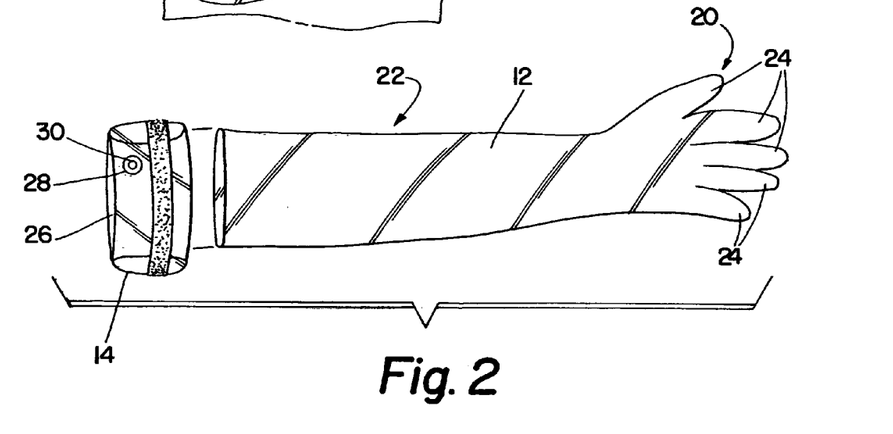
FIG. 2 is a perspective view showing a cover and an inflatable ring according to one embodiment of the present invention.

The arm cover assembly 10 is shown in FIG. 2. As can be seen, the glove 12 includes a hand portion 20 and a sheath portion 22. The preferred arrangement for the hand portion 20 includes with individual finger portions 24 that permit maximum dexterity for a user. It should be appreciated that a mitten-type hand portion (not shown) that includes only a thumb portion and a hand portion 20 could be substituted. Similarly, the hand portion that includes individual finger portions 24 could be replaced with a bag-like portion (not shown) that does not include any finger portions 24.

The glove 12 should be made from a flexible waterproof material. The preferred material is a transparent polypropylene. Colored and opaque materials, or materials with a decorative pattern may also be used. Those of skill in the art will be aware of a wide variety of waterproof flexible materials that would be suitable for forming the glove. The finger portions 24 may be reinforced to prevent breakage. The finger portions 24 and palm side of the hand portion 20 may be provided with texture (not shown) to improve the gripping characteristics of the glove 12.

Various sizes for the hand portion 20 and sheath portion 22 may be used. The portions should be large enough so that they will slide easily over the hand and cast 18. The sheath portion 22 is preferably long enough to reach to at least a typical users arm pit, or even longer. Any excess material on the sheath portion 22 can be trimmed off by a user if it is too long for that user's needs. The glove 12 may be made in a left hand and right hand version with the thumb portion biased towards the palm side, or, the thumb portion may be neutral so that a single style will work for either hand.

Figure 3:
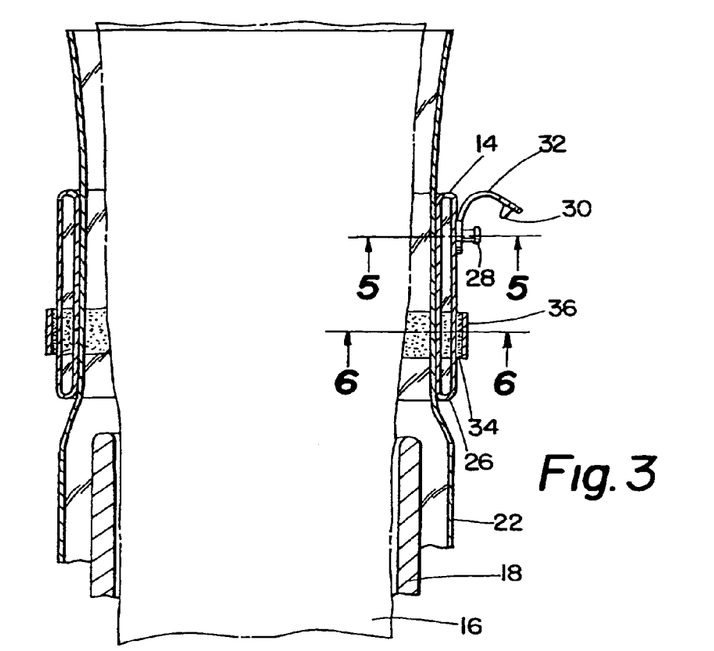
FIG. 3 is a partial cross-sectional view taken along line 3—3 of FIG. 1, showing the inflatable ring in a deflated condition.
Figure 4:
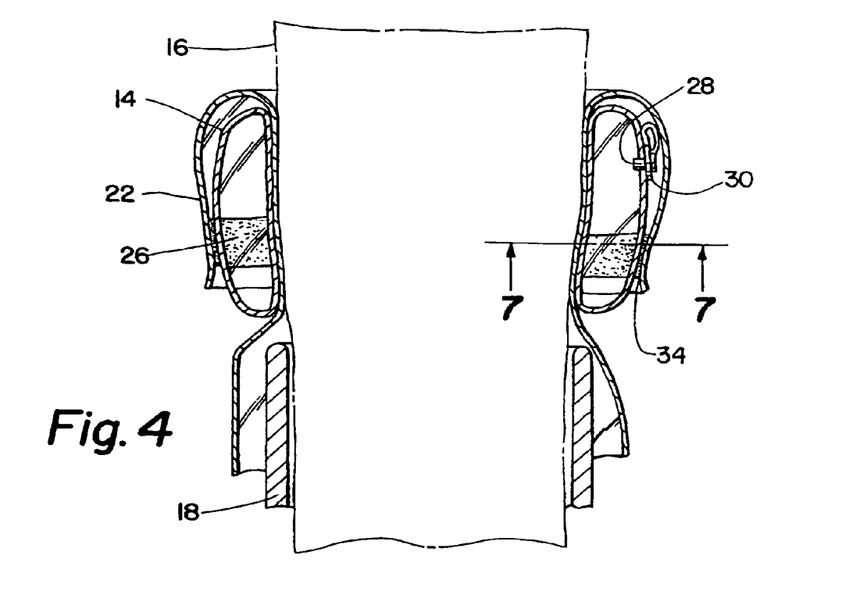
FIG. 4 is a partial cross-section view taken along line 4—4 of FIG. 1, showing the inflatable ring in a sealed inflated condition.
Figure 5:
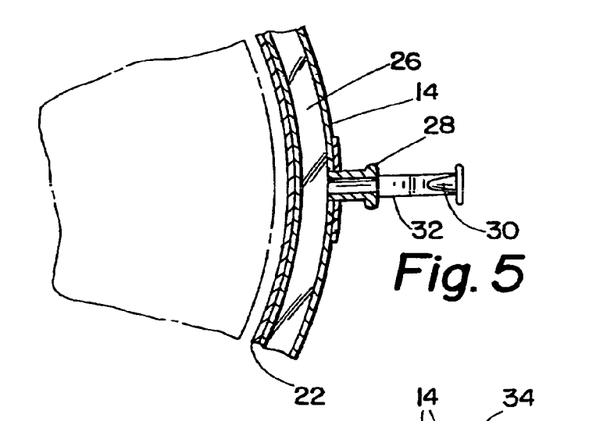
FIG. 5 is a cross-sectional view of the cover and inflatable ring of FIG. 1 taken along line 5—5 of FIG. 3.

The inflatable ring 14 includes an airtight bladder 26 with a generally toroidal shape. A valve 28 is provided so that a user can pressurize the bladder 26, typically with air. In the embodiment of FIGS. 1–4, the valve 28 has an associated plug 30 that is inserted into the valve to close and seal the bladder, and which plug 30 is removable from the valve 28 to permit inflating and deflating of the bladder 26. The plug 30 is retained on the ring 14 when not inserted into the valve 28 by a flexible tether 32. The valve 28 is of the type commonly found on inflatable toys that can be pulled outward to extend outwardly (see FIG. 3) from the ring 14 to permit filling and can be pushed inward (see FIG. 4) so that it is nearly flush with the wall of the ring 14 during use. To inflate the bladder 26, a user extends the valve 28 (FIG. 3) and blows air through the valve 28 either by covering with the mouth and blowing, or by using a pump. After the desired pressure has been achieved in the bladder 26, the plug 30 is inserted into the valve 28, and the is pushed to its inward storage position (FIG. 4). Those of skill in the art will be aware of various other designs for valves that would be equally suitable.

The inflatable ring 14 should be sized to slip easily over the user's arm 16 and cast 18 when not inflated, but such that it will fit snuggly against the user's arm 16 when inflated. The ring 14 should have an airtight bladder 26, and should be water resistant such that it will not take on water or deteriorate in water. Personal floatation devices, sometimes colloquially referred to as "floaties" or "water wings" may be well suited for the purpose, and are the preferred form of the rings 14.

Figure 6:
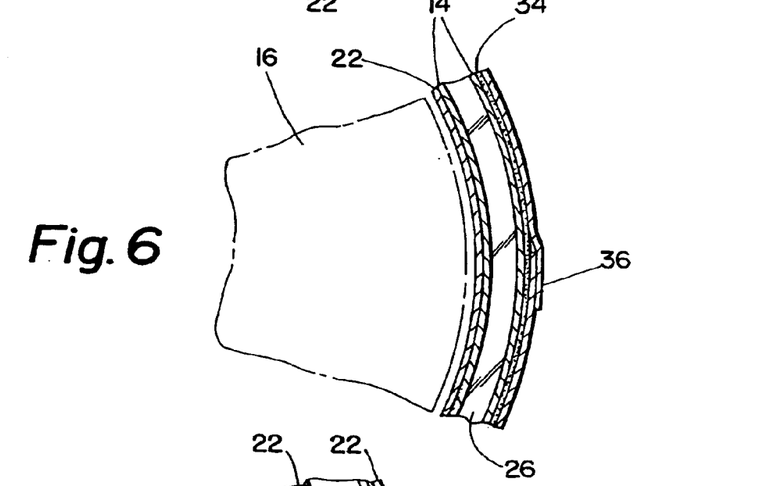
FIG. 6 is a cross sectional view of the cover and inflatable ring of FIG. 1 with the ring in a deflated condition taken along line 6—6 of FIG. 3.
Figure 7:
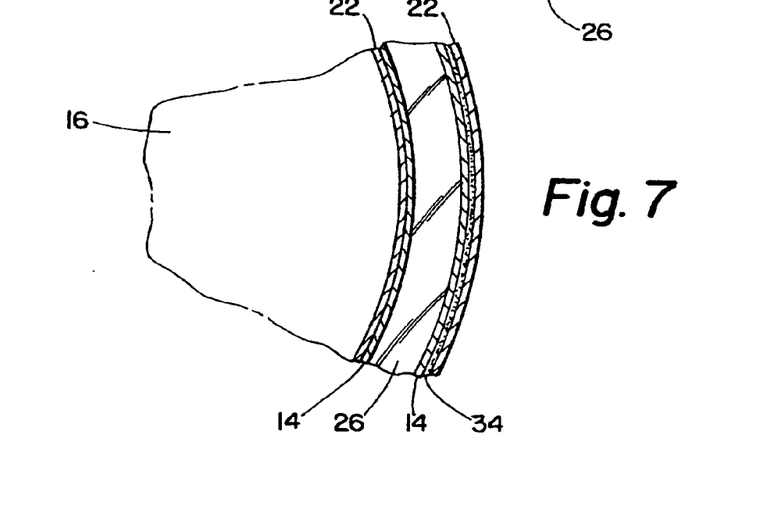
FIG. 7 is a cross sectional view of the cover and inflatable ring of FIG. 1 with the ring in an inflated condition taken along line 7—7 of FIG. 4.

The inflatable ring 14 may include an adhesive strip 34 along its outside surface. This adhesive strip is preferably formed by a contact adhesive that will stick to and retain the free end of the sheath when pressed against it. Preferably the adhesive will be of the type that will permit the free end of the sheath portion 22 to be stuck and unstuck from the ring 14 at least a few times. In other words, the holding power of the adhesive 34 should be sufficiently strong to retain the free end of the sheath 22 in place, but should be weak enough to permit the sheath portion 22 to be unstuck without ripping or tearing. A removable disposable covering strip 36 (see FIG. 6) may be provided on the adhesive strip 34 before use. The covering strip 36 can be pulled off to expose the adhesive strip 34 after the ring 14 is in place on the user's arm.

In use, a user's arm 16 is inserted into the glove 12 such that the user's fingers engage the corresponding finger portions 24 of the glove 12. The sheath portion 22 is pull up to completely over the cast 18, or other portion of the arm that needs to be protected. The inflatable ring 14 can then be slid up the arm 16 until it is at a location above, or distal to, the area that needs to be protected. This arrangement is shown in FIG. 3. Once the ring 14 is in the desired position above the cast 18 it can be inflated. Inflation can be accomplished by covering the valve 28 with a mouth and blowing air into the bladder 26, or by using a pump 40 (see FIG. 13). The ring 14 should be inflated to a pressure sufficient to hold the sheath portion 22 tightly against the users arm 16 to form a barrier against water or other contaminants getting to the cast 18. The pressure should not be so high as to be uncomfortable or cut off blood circulation in the user's arm 16. Once the ring 14 has been inflated to the desired pressure, the plug 30 should be inserted into the valve 28 to form an airtight seal. The valve 28 can then be pushed into the ring 14 to the position shown in FIG. 4.

Preferably a portion of the sheath portion 22 will extend past the top of the ring. This excess portion of the sheath portion 22 can be stuck to the adhesive strip 34, as shown in FIG. 4, to provide a neat appearance, and to keep the ring 14 from slipping up off of the sheath portion 22. If too much sheath portion 22 extends beyond the top of the ring 14, a user may desire to trim some of the excess portion off using scissors of the like. Because a user can easily shorten a sheath portion 22 to the desired length, it is desirable to provide the sheath portion 22 a sufficient length to fit long arms.

With the inflated ring 14 in place as shown in FIGS. 1 and 4, the portion of the arm 16 that is distal to ring 14 is a protected portion. The sheath and hand portions 22 and 20 of the glove 12 provides a waterproof barrier around the protected portion that prevents the cast 18 from being contaminated. The ring 14 provides an upper seal that prevents water or other contaminants from entering the protected area through the open end of the glove 12. If desired, petroleum jelly, or similar product, can be applied around the user's arm 16 at the location where the ring 14 engages the sheath 22 to provide an even tighter seal. However, for general use in the bathtub or shower, no such application is generally needed. A user may adjust the pressure in the ring 14 if is too high, by partially removing the plug 30 from the valve 28 to release some air. Similarly, if the ring 14 begins to lose pressure, the user can simply add more air through the valve 28 to reinflate the ring 14 to the desired pressure.

The arm cover assembly 10 can therefore be quickly and easily applied, to provide a waterproof barrier that protects a portion of a user's arm. The assembly 10 is economical and can be made in various sizes to fit any user. Removal of the device is similarly simple. The end of the sheath 22 is removed from the adhesive strip 34. The valve 28 is pulled outward to its extended position, and the plug 30 is removed from the valve 28. The ring 14 is allowed to deflate, and can then be pulled off of the user's arm. The glove 12 can also be simply pulled off the arm 16 to reveal the dry clean cast 18. The same ring 14 can be re-used with additional gloves 12.

Figure 8:
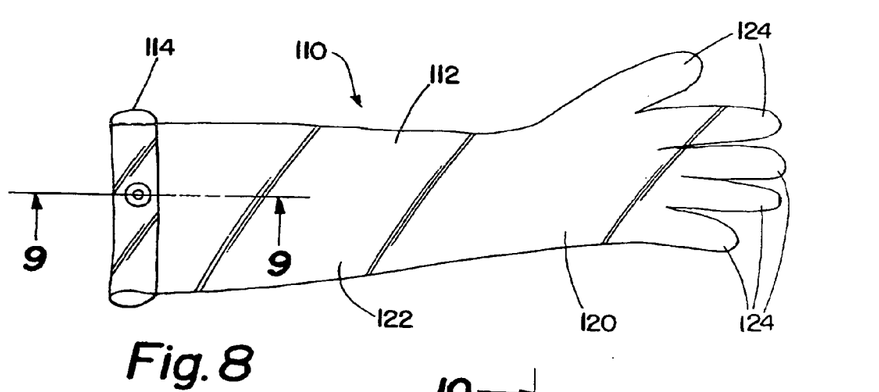
FIG. 8 is a perspective view of an arm cover including an inflatable ring according to an embodiment of the present invention.
Figure 9:
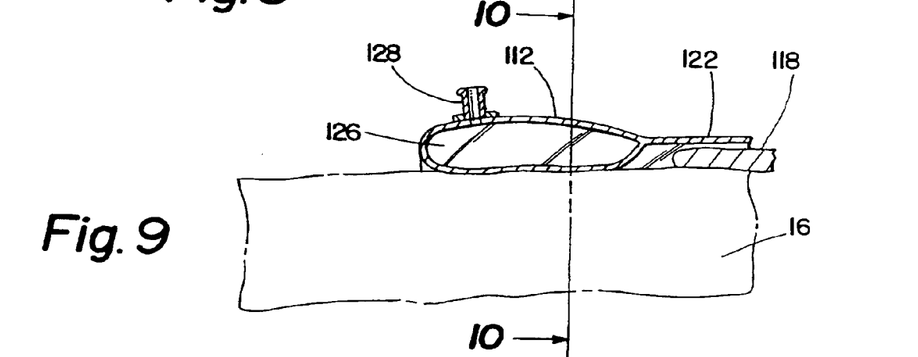
FIG. 9 is a partial cross sectional view of the arm cover of FIG. 8 in place on an arm, taken along line 9—9.
Figure 10:
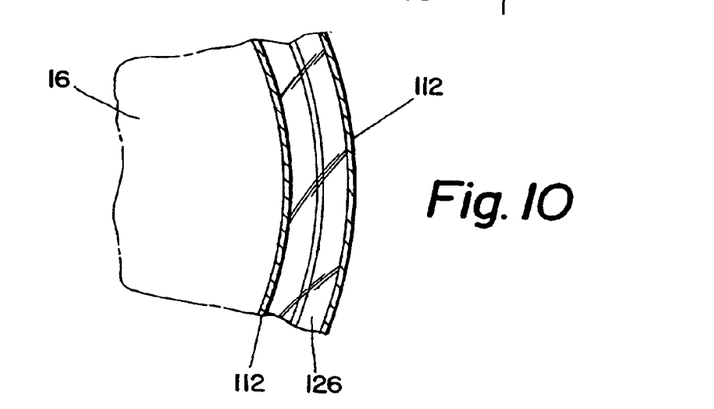
FIG. 10 is a partial cross sectional view of the arm cover of FIG. 8, taken along line 10—10 of FIG. 9.

A second embodiment of the invention is shown in FIGS. 8–10. According to this embodiment an arm cover 110 includes a waterproof glove 112 that includes a hand portion 120 and a sheath portion 122. An inflatable ring 114 is attached to an open end of the sheath portion 122 opposite from the hand portion 120. The primary difference between the embodiment of FIGS. 8–10 and the embodiment previously described relative to FIGS. 1–7, is that the inflatable ring 114 is affixed to the sheath portion 122 permanently. It should be affixed such that the seam between the ring 114 and the sheath 122 is watertight. Methods of attachment may include adhesive tape, welding, or glue or other similar adhesives. Those of ordinary skill in the art will be aware of numerous acceptable means of attaching the ring 114 to the sheath 122 in a watertight manner. This arrangement has the advantage of providing the entire assembly in a single piece, but has the disadvantage of having somewhat less flexibility in sizing the sheath portion 122.

In use, the user's arm 16 is inserted through the uninflated ring 114 until the user's fingers are engaged in the corresponding finger portions 124 of the glove 112. The inflatable ring 114 is located on the user's arm 16 somewhere proximal, or above, the portion of the arm 16 to be protected, generally a cast 18. The inflatable ring 114 is then inflated to a desired pressure by adding air to the inflatable bladder 126 through a valve 128. The ring 114 pressing against the arm 16 creates a barrier that is sufficient to prevent water, or other contaminants, from getting into the protected area. The desired pressure is that which is sufficient to create a watertight seal, but not so tight as to be uncomfortable or unduly restrict circulation in the user's arm 16. It is preferable that the ring 114 be in direct contact with the user's skin, rather than with a shirt or other impediment. It can however, be desirable to apply a coat of petroleum jelly or similar material to the user's arm to help in forming a watertight seal. Application of petroleum jelly is generally not necessary for light uses such as bathing or showering.

Various sizes of cover 110 can be made depending on the expected use. It can be sized for children, adolescents or adults. It may also be desirable to provide different lengths of the sheath portion 122 depending on the expected use. For example, a much shorter sheath portion 122 is needed if the cover 110 is expected to be used to cover a wrist cast, as opposed to a full arm cast.

Figures 11, 12, 13:
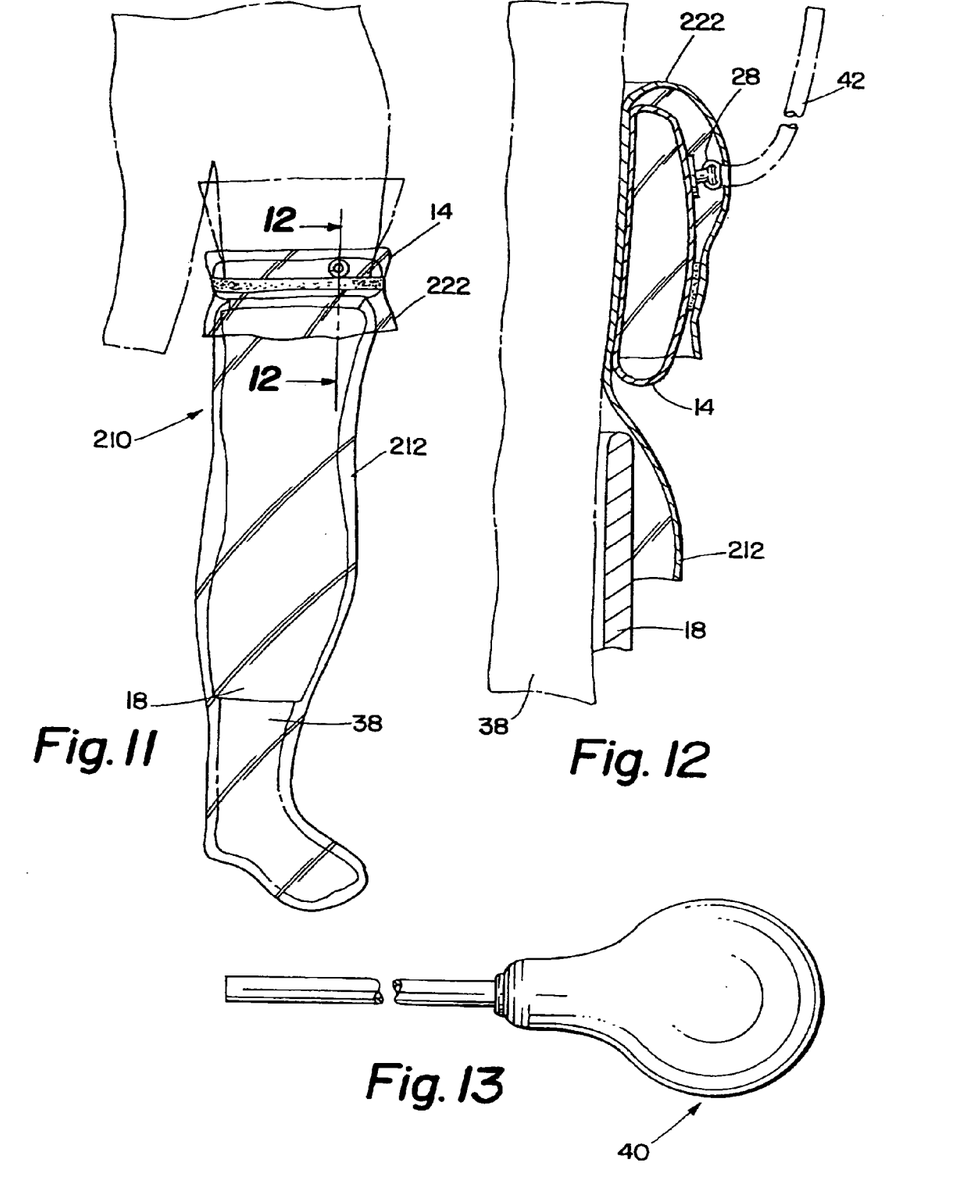
FIG. 11 is a perspective view of a leg cover and inflatable ring according to another embodiment of the present invention.
FIG. 12 is a partial cross sectional view of the leg cover and inflatable ring of FIG. 11 taken along line 12—12 of FIG. 11, along with a flexible inflation tube according to one embodiment of the present invention.
FIG. 13 is a perspective view of a hand pump that is suitable for use in inflating the inflatable ring of the present invention.

A third embodiment of the invention is shown in FIGS. 11 and 12. This embodiment relates to a leg cover assembly 210. The leg cover assembly 210 includes an inflatable ring 14 and a waterproof stocking 212. The waterproof stocking 212 includes an enclosed lower foot portion 220 and an open upper sheath portion 222. The bottom of the foot portion 222 may be provided with reinforcement and traction means such as a tread or studs and the like (not shown). The waterproof stocking 212 should be made from a flexible waterproof material such as polypropylene or the like. Those of skill in the art will be aware of numerous acceptable materials for forming the waterproof stocking 212. The inflatable ring 14 should be as described above, however, it may need to be larger in diameter to accommodate a leg 38 rather than an arm 16.

In use, a user's leg 38 is inserted into the stocking 212 so that the end of the sheath portion 222 extends above the cast 18 other portion to be protected. The uninflated ring 14 is pulled over the stocking 212 to a location above the cast 18, to the position shown in FIG. 11. The ring 14 is then inflated to a desired pressure to hold the sheath portion 222 in tight contact with the user's leg 38, and thereby create a barrier that prevents water, and other contaminants from getting into the protected area below the ring 14. Because of the location of the ring 13 on the user's leg 38, the valve 28 will generally not be accessible to the user's mouth. Therefore, different means must be used to inflate the ring 14. A hand pump 40 may be attached to the valve 28 to aid in inflating the ring 14. Alternatively a long flexible tube 42 that will engage the valve 28 as shown in FIG. 12 may be used. The long flexible tube may extend to the user's mouth so that a pump is not needed to inflate the ring 14.

After the ring 14 has been inflated to the desired pressure, the portion of the sheath 222 that extends over the ring 14 may be folded over and adhered to the adhesive ring 34. This creates a neater appearance for the assembly 210, and helps to prevent the ring 14 from slipping off of the sheath 222. Excess sheath may be trimmed off using a scissors or the like for persons with shorter legs. A protected area is provided at the distal end of the leg 38 below the ring 14. The assembly 210 can be easily removed by pulling the sheath portion 222 off of the adhesive 34, deflating the ring 14 and slipping the ring 14 and stocking 212 off of the leg to reveal the dry clean cast.

Therefore, a cover that is well suited for use in protecting arms and legs in casts has been described. It is comfortable to wear, easy to attach, and economical to use. It allows a user that has a cast to takes baths and showers without getting the cast wet or otherwise contaminated.

Although the present invention has been described with a certain degree of particularity, it is understood that the disclosure has been made by way of example, and changes in detail or structure may be made without departing from the spirit of the invention as defined in the appended claims.

I claim:

1. A cover assembly for protecting a portion of a user's anatomy, the cover comprising:
    a waterproof sheath having an open end for receiving a portion of a user's anatomy; and
    an inflatable ring for mating engagement with the portion of the user's anatomy such that when said inflatable ring is not inflated said inflatable ring is slidably adjustable to a desired location relative to said open end of said waterproof sheath, and when said inflatable ring is inflated, a barrier is formed by said inflatable ring in combination with said waterproof sheath to resist water and other contaminants and thereby substantially protect the portion of the user's anatomy from contamination.

2. The cover assembly of claim 1, wherein the sheath is shaped to receive a user's arm.

3. The cover assembly of claim 2, wherein the sheath includes separate portions for receiving a user's fingers.

4. The cover assembly of claim 1, wherein the sheath is shaped to receive a user's leg.

5. The cover assembly according to claim 1, wherein said barrier is formed by said inflatable ring being inflated to a sufficient pressure to hold a portion of said sheath in close engagement with the user's anatomy.

6. The cover assembly according to claim 5, wherein said inflatable ring further comprises an adhesive portion for adhering to said sheath when said inflatable ring is inflated.

7. The cover assembly according to claim 6, further comprising a removable disposable cover strip on said adhesive portion.

8. The cover assembly according to claim 1, wherein said inflatable ring comprises a retractable valve.

9. A method of protecting a portion of a user's limb:
    inserting the user's limb into a water proof sheath, said water proof sheath including an open end and a close end, said water proof sheath covering and enclosing a portion of the limb;
    placing an inflatable ring, in an at least partially deflated condition, over the sheath proximate to said open end, and adjusting said at least partially deflated inflatable ring to a desired location relative to said open end;

inflating said inflatable ring to hold said waterproof sheath in close contact with said limb and thereby form a barrier to resist water and other contaminants from reaching the protected portion of the limb distal from said inflated inflatable ring.

10. The method according to claim 9, wherein said protected portion includes a cast.

11. The method according to claim 9, further comprising adhering a portion of said sheath to an adhesive portion provided on said inflatable ring.

12. The method according to claim 9, wherein the limb is an arm, and further wherein the sheath comprises a glove.

13. The method according to claim 9, wherein the limb is a leg, and further wherein the sheath comprises a stocking.

14. A cover assembly for protecting a portion of a user's anatomy, the assembly comprising:

an impermeable sheath having an open end for receiving a portion of a user's anatomy and a closed end opposite from said open end; and an inflatable sealing ring for mating engagement over the portion of the user's anatomy and the sheath such that when said sealing ring is inflated, a barrier is formed by said inflated sealing ring in combination with said impermeable sheath to resist water and other contaminants and thereby form a protected portion of the user's anatomy between said inflated sealing ring and said closed end, said inflatable sealing ring being adjustable to a desired location relative to said sheath to adjust a length of said protected portion.

15. The cover assembly of claim 14, further comprising an adhesive strip on said inflatable sealing ring for selectively adhering said impermeable sheath to said inflatable ring.

16. The cover assembly of claim 15, wherein a removable disposable cover strip is provided on said adhesive strip.

17. The cover assembly of claim 15, wherein said adhesive strip is provided on an outward facing surface of said inflatable sealing ring for adhering to an overhanging folded over portion of said impermeable sheath proximate to said open end of said impermeable sheath.

* * * * *